United States Patent [19]

Shankel

[11] Patent Number: 4,904,875
[45] Date of Patent: Feb. 27, 1990

[54] FACIAL TISSUE SPLICE DETECTOR SYSTEM

[75] Inventor: Richard Shankel, Antioch, Calif.

[73] Assignee: James River Corporation, Richmond, Va.

[21] Appl. No.: 303,928

[22] Filed: Jan. 30, 1989

[51] Int. Cl.⁴ .......................... G01N 21/64; B07C 5/00
[52] U.S. Cl. ................... 250/461.1; 250/302; 250/458.1; 250/459.1; 209/576
[58] Field of Search ............... 250/302, 458.1, 459.1, 250/461.1; 226/45, 10; 209/576-579

[56] References Cited

U.S. PATENT DOCUMENTS

| 3,967,994 | 7/1976 | Langberg | 242/58.4 |
|---|---|---|---|
| 4,583,669 | 4/1986 | Sirkis | 226/45 |
| 4,746,020 | 5/1988 | Schenk | 226/45 |
| 4,752,684 | 6/1988 | Herrmann | 250/302 |
| 4,828,156 | 5/1989 | Whiteley et al. | 226/45 |

*Primary Examiner*—Carolyn E. Fields
*Attorney, Agent, or Firm*—Thomas R. Lampe

[57] ABSTRACT

A system for detecting a splice in a single facial tissue in a stack of facial tissues wherein a detector agent is applied at the location of the splice, the facial tissue is folded so that the detector agent is located at least one side edge thereof, and detecting the existence of the detector agent at the side edge to actuate a reject mechanism.

7 Claims, 2 Drawing Sheets

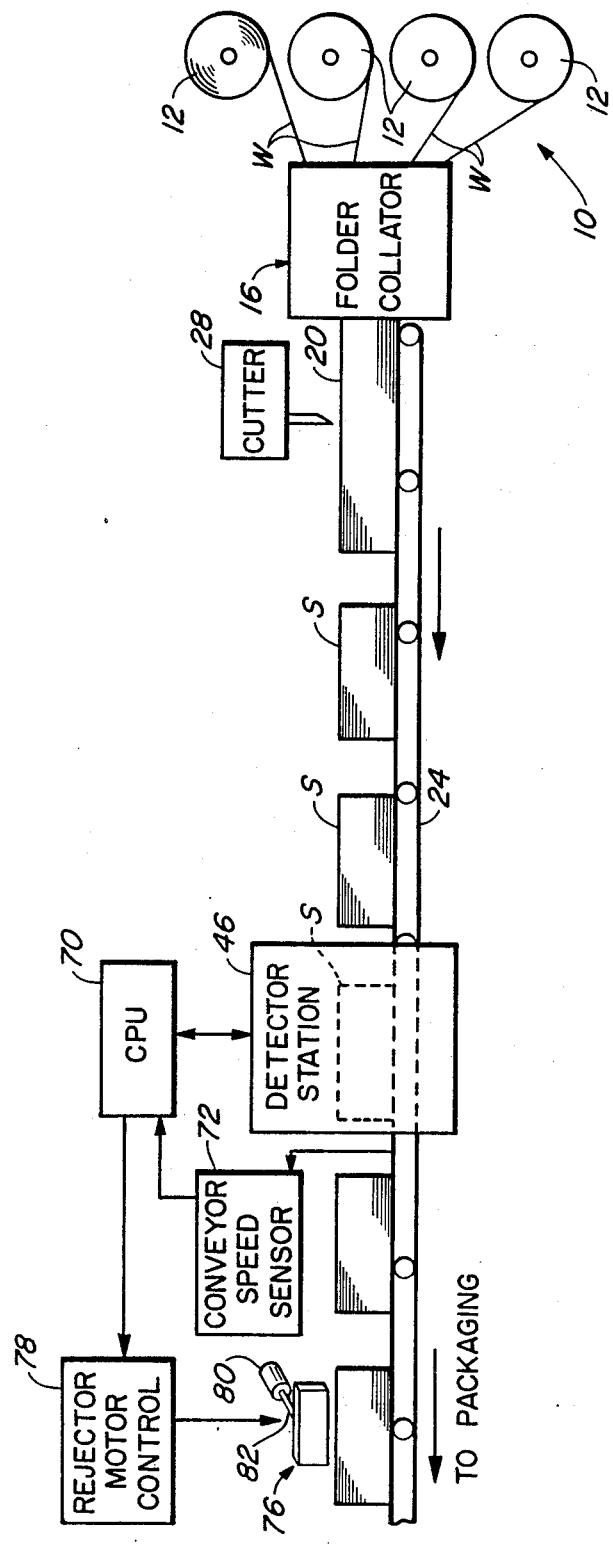
FIG._1.

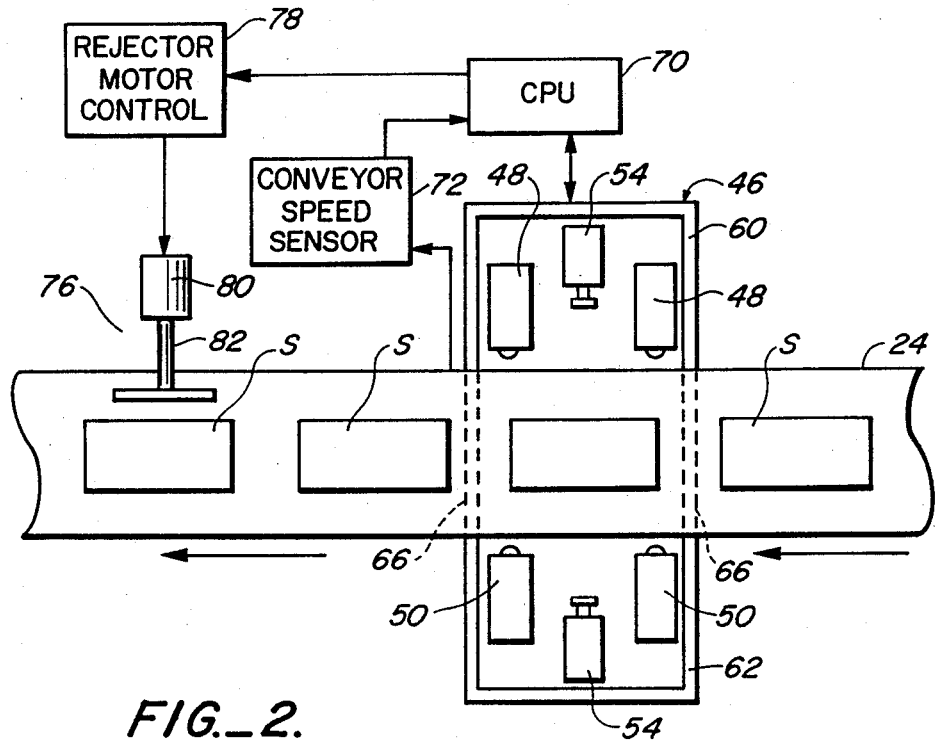
FIG._2.
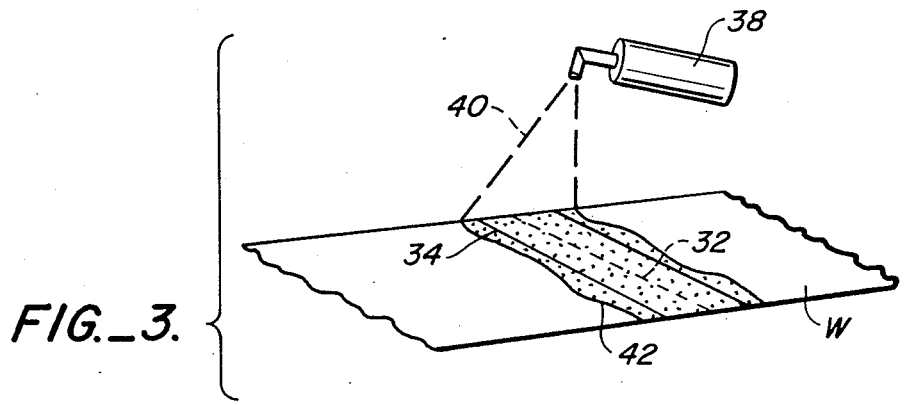
FIG._3.

FACIAL TISSUE SPLICE DETECTOR SYSTEM

TECHNICAL FIELD

This invention relates to a method and apparatus for detecting a splice in a single facial tissue in a stack of discrete facial tissues. In particular, the system of the present invention is incorporated in a facial tissue manufacturing operation and enables the manufacturer to readily and effectively detect stacks of facial tissue having one or more spliced tissues therein and rejecting such stack before it is packaged.

BACKGROUND ART

A conventional facial tissue manufacturing line includes an unwind station incorporating large numbers of tissue web parent rolls, often one hundred or more. A web of tissue is unwound from each of these parent rolls and passed through a folder station which consists of a plow mechanism which folds each of the tissue webs and positions them on top of one another in stacked relationship. If desired, the webs may be interfolded during stacking. The folded stacked webs of tissue are then cut to provide individual stacks of discrete facial tissues which are subsequently boxed or packaged in some other manner.

The tissue webs from which the facial tissues are manufactured often include splices. Typically, such splices are made by splicing tape and it is highly undesirable for the splice to end up in the final packaged product furnished to the consumer.

To ensure that spliced facial tissue is not packaged and sold, a common practice has been simply not to splice parent roll breaks. A conventional detector system detects unspliced parent rolls as web breaks and the entire line is shut down for each break. This results in high-production cost and a great deal of wasted product.

DISCLOSURE OF THE INVENTION

According to the teachings of the present invention, an apparatus and method are provided wherein a splice is detected in a single facial tissue in a stack of discrete facial tissues disposed in engagement and having generally aligned side edges. The stack is then rejected and not forwarded on to the final packaging operation. The system of the invention allows a splice to be made upstream from the detecting station and additionally allows for continued operation of the facial tissue line with assurance that a spliced product will not be delivered to the consumer.

In summary, the method of the present invention includes the steps of, prior to formation of a facial tissue from a tissue web, applying a detector agent to the tissue web at the location of a splice in the web. During formation of the facial tissue incorporating the splice, such tissue is folded so that the detector agent is located at at least one side edge of the facial tissue.

The facial tissue incorporating the splice and detector agent is incorporated in a stack of tissues, the stack then being transported to a detector station. At the detector station, the existence of the detector agent is detected whereby the stack incorporating the splice and detector agent may subsequently be rejected prior to packaging thereof.

Other features, advantages and objects of the present invention will become apparent with reference to the following detailed description and accompanying drawings.

BRIEF DESCRIPTION OF DRAWINGS

FIG. 1 is a diagrammatic side view illustrating apparatus incorporating the teachings of the present invention;

FIG. 2 is a diagrammatic plan view illustrating a preselected portion of such apparatus; and FIG. 3 is a diagrammatic perspective view illustrating a typical web splice and the application of a detector agent thereto.

BEST MODE FOR CARRYING OUT THE INVENTION

Referring now to the drawings, in FIGS. 1 and 2 there is a diagrammatic presentation of a facial tissue converting line which incorporates the teachings of the present invention. In the drawings, product flow is from right to left.

Reference numeral 10 generally designates a plurality of parent rolls 12, each said parent roll being formed of overlying convolutions of tissue web W. It will be appreciated that each parent roll 12 is mounted for rotation on a back stand of a type typically employed in facial tissue converting operations. Since the back stand itself does not form part of the present invention and such devices are well known, it has not been illustrated. Suffice it to say that each back stand can support for rotational movement thereon a great many parent rolls. It is not unusual, for example, for a back stand array to rotatably support one hundred or more parent rolls. Only four such parent rolls are shown in FIG. 1 for the purposes of simplicity.

The webs W converge as they are unwound from the parent rolls and converge at a folder collator device 16 which is also conventional and may be of any suitable type. A suitable folder collator is manufactured by Paper Converting Machine Company of Green Bay, Wisconsin.

Folder collator device 16 folds and combines the webs W so that the webs are in stacked relationship. It is common for folder collator devices to also interfold the webs W. Alternatively, the folded webs may simply be stacked in face-to-face relationship and not interfolded. In any event, when the webs W emerge from folder collator device 16 they are in the form of a continuous elongated stack 20 disposed by the top run of a conveyer 24 which transports the continuous, elongated stack 20 to the left as indicated by the arrows.

As the stacked and folded webs W move to the left as shown in FIGS. 1 and 2, they pass by a cutter device 28 which severs the webs so that they form individual stacks S of discrete facial tissues disposed in engagement and having generally aligned side edges. Again, cutter devices for such purpose are old in the art and will not be described in detail. Any form of prior art cutting device may be employed to form the individual stacks, such as devices incorporating saws, reciprocal cutting blades and the like. One suitable cutting device for performing the desired function is a multiple cutoff saw manufactured by Paper Converting Machine Company of Green Bay, Wisconsin.

It will be appreciated that one or more of the webs W when unwound from parent rolls 12 may have a splice formed therein. FIG. 3 illustrates a portion of a web W with a typical splice. Splices typically are formed when a web breaks or when the tail end of one web section is secured to the lead end of another web section. The splice may be formed at any location upstream from the folder collator device, either prior to formation of the parent roll or during the unwinding of the web W therefrom.

In FIG. 3 a break between two web sections is shown in phantom and designated by reference numeral 32. Typically, the splice is made by adhesive tape 34 which extends across the full width of web W. Many types of equipment and procedures exist for forming splices on paper webs and the particular approach utilized forms no part of the present invention. What does, however, form part of the present invention and is distinguished from prior art approaches is the step illustrated in FIG. 3 of applying a detector agent to the tissue web at the location of the splice in the web.

Typically, this application step will be carried out at the time the splice is made. One particular approach for accomplishing this is shown. In FIG. 3 a hand held aerosol can or container is manipulated by an operator so that it sprays a suitable detector agent 40 on to the web along the length of tape 34 and on both sides thereof as indicated by reference numeral 42.

The detector agent 40 utilized in the disclosed preferred mode of the invention is a liquid ultraviolet agent which is normally invisible to the naked eye but is fluoresced by exposing the detector agent to ultraviolet light. One suitable such agent is LEUCOPHOR BCR made available by SANDOZCHEMICALS, Charlotte, North Carolina. It is important that the agent not normally be visible to the naked eye under ordinary light since it is possible that the agent may be inadvertently applied to some portions of the web W not in the immediate vicinity of the splice. A consumer using a package of tissue containing some of this overspray or misdirected spray obviously will not see it if the agent is observable only under ultraviolet light.

Since the sprayed area 42 extends across the width of the web W, some of the detector agent is located at at least one side edge of a folded facial tissue after formation of a stack. It is important that the detector agent be located at at least one side edge of the spliced facial tissue since the apparatus which will now be described for detecting the existence of the agent senses from the side of a stack which typically contains one hundred or more discrete facial tissues.

Referring once again to FIGS. 1 and 2, detection is accomplished at a detector station 46. The detector station includes two pairs of ultraviolet light sources 48, 50, one such pair being disposed along one side of conveyer 24 and the other such pair being disposed on the other side, as illustrated. Positioned between the ultraviolet light sources of each pair thereof is a TV camera (FIG. 2) of a commercial vision system. The TV cameras and ultraviolet sources are disposed in housings 60, 62 which serve to block the ultraviolet light sources and TV cameras from ambient light. Further blockage of outside light is accomplished by flap curtains 64, 66 of conventional construction extending between the housings. As is conventional, the flap curtains are readily deformed by stacks S passing therethrough.

Ultraviolet light from sources 48, 50 will fluoresce detector agent 40 located at a side fold of a tissue. This can occur at one or both sides of a stack. In any event, when one or both of the TV cameras 54 detects fluorescence, a signal will be sent to a central processing unit 70 in the form of a micro computer. The central processing unit 70 also receives a signal from a step register 72 of any suitable type which continually monitors the conveyer 24.

The stack S containing the facial tissue with a splice continues on through the detector station, the conveyer 24 moving in step fashion. At the same time that particular stack S reaches the vicinity of a reject station 76, the central processing unit 70 will send a signal to detector motor control 78. Detector motor control 78 will actuate motor 80 to extend a push arm 82 to eject the stack incorporating a tissue with detector agent therein off of conveyer 24.

I claim:

1. A method for detecting a splice in a single facial tissue in a stack of discrete facial tissues disposed in engagement and having generally aligned side edges, each said facial tissue in said stack being formed from a different tissue web having a predetermined width, said method comprising the steps of:
   prior to formation of said single facial tissue from a tissue web, applying a detector agent invisible to the unaided eye to said tissue web at the location of a splice in said tissue web; said detector agent being applied across the full width of said tissue web;
   during formation of said single facial tissue, folding said single facial tissue so that said detector agent is located at at least one side edge of said single facial tissue;
   incorporating said single facial tissue in said stack so that said at least one side edge having the detector agent thereon is in general alignment with the side edges of the other facial tissues in said stack;
   transporting the stack of facial tissues including the single facial tissue to a detector station; and
   at said detector station, detecting the existence of said detector agent at at least one side edge of said single facial tissue, said detecting step including the steps of fluorescing said detector agent and sensing the fluorescence of said detector agent at said detector station.

2. The method according to claim 1 including the additional step of rejecting the stack responsive to the sensing of said fluorescence.

3. The method according to claim 1 wherein said detector agent is an ultraviolet agent applied to said tissue web in liquid form, said step of fluorescing said detector agent comprising exposing said detector agent to ultraviolet light.

4. The method according to claim 3 including the step of simultaneously directing said ultraviolet light toward opposed side edges of said stack of discrete facial tissues.

5. The method according to claim 2 wherein said rejecting step is carried out after said sensing step and at a location removed from said detector station.

6. Apparatus for detecting a splice in a single facial tissue in a stack of discrete facial tissues disposed in engagement and having generally aligned side edges, said single facial tissue having an ultraviolet responsive detector agent not visible to the unaided eye at the location of said splice and at at least one edge thereof, said apparatus comprising:
   means for transporting said stack along a predetermined path of movement;
   means for fluorescing said detector agent located along said predetermined path of movement, said fluorescing means comprising a pair of ultraviolet light sources disposed along said path of movement for directing ultraviolet light at all facial tissue edges on two opposed sides of said stack;

sensing means including a vision system for detecting the florescence of said detector agent caused by said fluorescing means;

rejecting means operatively associated with said sensing means for rejecting said stack in response to the sensing of said fluorescence;

control means operatively associated with said vision system and with said rejecting means, said control means being operable to receive a signal from said vision system in response to detection of detector agent fluorescence and to operate said rejecting means in response to reception of said signal; and enclosure means, said fluorescing means and said vision system positioned in said enclosure means and said enclosure means preventing substantially all ambient light from reaching said fluorescing means and said vision system.

7. The apparatus according to claim 6 wherein said control means includes a step register in operative association with said transporting means.

* * * * *